US012808881B2

(12) United States Patent
Chang et al.

(10) Patent No.: US 12,808,881 B2
(45) Date of Patent: Nov. 24, 2026

(54) BETA2-MICROGLOBULIN CONCENTRATION ANALYZING METHOD AND DEVICE

(71) Applicant: INDUSTRIAL TECHNOLOGY RESEARCH INSTITUTE, Hsinchu (TW)

(72) Inventors: Ching-Hsuan Chang, Taichung City (TW); Pi-Ju Fu, Taoyuan City (TW); Fang-Hsin Lin, Taichung City (TW); Kuan-Hung Liu, Taichung City (TW); Bin Hsu, Tainan City (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 851 days.

(21) Appl. No.: 18/096,447

(22) Filed: Jan. 12, 2023

(65) Prior Publication Data

US 2023/0324409 A1 Oct. 12, 2023

Related U.S. Application Data

(60) Provisional application No. 63/329,043, filed on Apr. 8, 2022.

(30) Foreign Application Priority Data

Aug. 26, 2022 (TW) ................................ 111132190

(51) Int. Cl.
*G01N 1/34* (2006.01)
*G01N 15/14* (2024.01)
(Continued)

(52) U.S. Cl.
CPC .......... *G01N 33/6872* (2013.01); *G01N 1/34* (2013.01); *G01N 15/1434* (2013.01);
(Continued)

(58) Field of Classification Search
CPC .. G01N 33/6872; G01N 1/34; G01N 15/1434; G01N 33/6848; G01N 35/0099;
(Continued)

(56) References Cited

U.S. PATENT DOCUMENTS 8,247,235 B2 8/2012 Caulfield et al.
9,638,705 B2 5/2017 Kalantar-Zadeh et al.

OTHER PUBLICATIONS

And Zhao et al. ("Direct preparation of dialysate from tap water via osmotic dilution," Journal of Membrane Science 598 (2020). (Year: 2020).*

(Continued)

*Primary Examiner* — Charles Capozzi
*Assistant Examiner* — Michael Stanley Gzybowski
(74) *Attorney, Agent, or Firm* — Maschoff Brennan

(57) ABSTRACT

A beta2-microglobulin concentration analyzing method includes: preparing a sample with dialysate, and putting the sample into a differential mobility analyzing device for analysis to obtain a beta2-microglobulin concentration. The present invention further provides a beta2-microglobulin concentration analyzing system, which includes: a preparation device and a differential mobility analyzing device, wherein the preparation device is configured to prepare a sample with dialysate, and the differential mobility analyzing device is configured to analyze the sample to obtain a beta2-microglobulin concentration.

7 Claims, 9 Drawing Sheets

(51) Int. Cl.
*G01N 15/1434* (2024.01)
*G01N 33/68* (2006.01)
*G01N 35/00* (2006.01)

(52) U.S. Cl.
CPC ..... *G01N 33/6848* (2013.01); *G01N 35/0099* (2013.01); *G01N 2015/1486* (2013.01); *G01N 2333/70539* (2013.01)

(58) Field of Classification Search
CPC . G01N 2015/1486; G01N 2333/70539; G01N 15/01; G01N 15/065
See application file for complete search history.

(56) References Cited

OTHER PUBLICATIONS

"Charge-reduced nano electrospray ionization combined with differential mobility analysis of peptides, proteins, glycoproteins, noncovalent protein complexes and viruses" Bacher et al., 2001.

"Elongated oligomers in β2-microglobulin amyloid assembly revealed by ion mobility spectrometry-mass spectrometry" Smith et al., Apr. 2010.

"Proteomics and Metabolomics in Kidney Disease, including Insights into Etiology, Treatment, and Prevention" Dubin et al., Dec. 2019.

"Review of applications of high-field asymmetric waveform ion mobility spectrometry (FAIMS) and differential mobility spectrometry (DMS)" Kolakowski et al., Oct. 2007.

Antoni J. H. Borysik, et al., "Separation of b2-microglobulin conformers by high-field asymmetric waveform ion mobility spectrometry (FAIMS) coupled to electrospray ionisation mass spectrometry," Rapid Commun. Mass Spectrom., vol. 18, pp. 2229-2234 (2004).

Mantas Malisauskas, et al., "Lability Landscape and Protease Resistance of Human Insulin Amyloid: A New Insight into Its Molecular Properties," J. Mol. Biol., vol. 396, pp. 60-74 (2010).

TW Office Action dated Sep. 1, 2023 as received in Application No. 111132190.

* cited by examiner

BETA2-MICROGLOBULIN CONCENTRATION ANALYZING METHOD AND DEVICE

CROSS-REFERENCE TO RELATED APPLICATIONS

This non-provisional application claims priority under 35 U.S.C. § 119(a) on Patent Application No. 63/329,043 filed in the U.S. on Apr. 8, 2022, and Patent Application No(s). 111132190 filed in Republic of China (ROC) on Aug. 26, 2022, the entire contents of which are hereby incorporated by reference.

BACKGROUND

1. Technical Field

This disclosure relates to a beta2-microglobulin concentration analyzing method and device.

2. Related Art

Examination reports of patients with end-stage renal disease often show excessive amount of uremic toxins accumulated in their body, and the concentration of beta2-microglobulin is regarded as one of the indicators for tracking accumulation of middle-molecule uremic toxins in patients with end-stage renal disease. Generally, labs use enzyme-linked immunosorbent assay (ELISA) to analyze the concentration of beta2-microglobulin in the specimen. However, the operation of ELISA requires intensive laboratory labor and expensive reaction reagents, which results in high costs for each test but the test result is often not obtained immediately.

SUMMARY

According to one or more embodiment of this disclosure, a beta2-microglobulin concentration analyzing method includes: preparing a sample with dialysate; and placing the sample into a differential mobility analyzing device for analysis to obtain a beta2-microglobulin concentration.

According to one or more embodiment of this disclosure, a beta2-microglobulin concentration analyzing method, adapted to a differential mobility analyzing device, wherein the differential mobility analyzing device includes an electrospray atomizer, a differential mobility analyzer and a condensation particle counter, and the method includes: inputting a sample prepared with dialysate into the electrospray atomizer to obtain an aerosol sample; inputting the aerosol sample into the differential mobility analyzer to obtain a screened particle sample; inputting the screened particle sample into the condensation particle counter to obtain a particle count; and dividing the particle count by a volume of the dialysate entered per unit time to obtain a beta2-microglobulin concentration.

According to one or more embodiment of this disclosure, a beta2-microglobulin concentration analyzing device includes: an electrospray atomizer configured to receive a sample prepared with dialysate and output an aerosol sample; a differential mobility analyzer configured to receive the aerosol sample and output a screened particle sample; and a condensation particle counter configured to receive the screened particle sample and output a particle count, wherein beta2-microglobulin concentration of the sample is obtained by dividing the particle count by a volume of the dialysate entered per unit time.

BRIEF DESCRIPTION OF THE DRAWINGS

The present disclosure will become more fully understood from the detailed description given hereinbelow and the accompanying drawings which are given by way of illustration only and thus are not limitative of the present disclosure and wherein.

DETAILED DESCRIPTION

In the following detailed description, for purposes of explanation, numerous specific details are set forth in order to provide a thorough understanding of the disclosed embodiments. According to the description, claims and the drawings disclosed in the specification, one skilled in the art may easily understand the concepts and features of the present invention. The following embodiments further illustrate various aspects of the present invention, but are not meant to limit the scope of the present invention.

Figure 1:
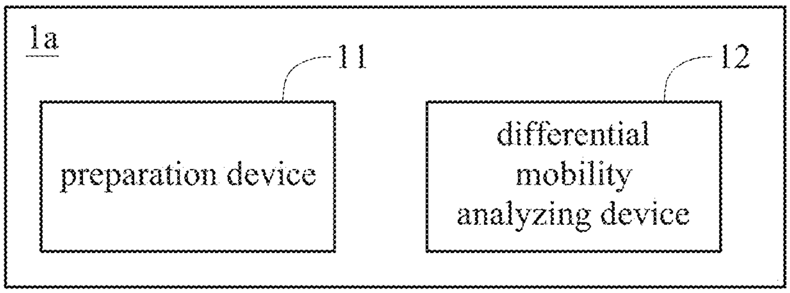
FIG. 1 is a block diagram illustrating a beta2-microglobulin concentration analyzing system according to an embodiment of the present disclosure.

Please refer to FIG. 1, wherein FIG. 1 is a block diagram illustrating a beta2-microglobulin concentration analyzing system according to an embodiment of the present disclosure. The beta2-microglobulin concentration analyzing system 1*a* includes a preparation device 11 and a differential mobility analyzing device 12. The preparation device 11 is configured to prepare a sample, the differential mobility analyzing device 12 is configured to analyze a concentration of the sample, wherein a process of transferring the sample prepared by the preparation device 11 to the differential mobility analyzing device 12 for analysis may be performed by laboratory personnel.

Figure 2:
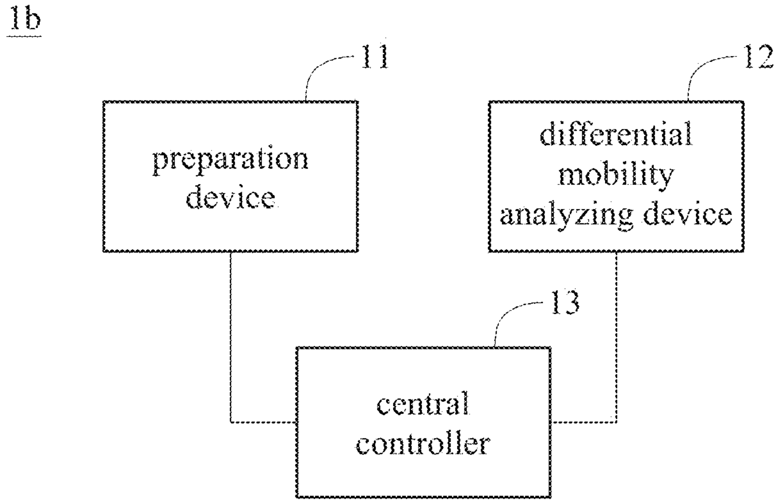
FIG. 2 is a block diagram illustrating a beta2-microglobulin concentration analyzing system according to another embodiment of the present disclosure.

Please refer to FIG. 2, wherein FIG. 2 is a block diagram illustrating a beta2-microglobulin concentration analyzing system according to another embodiment of the present disclosure. The beta2-microglobulin concentration analyzing system 1*b* shown in FIG. 2 includes the preparation device 11, the differential mobility analyzing device 12 and a central controller 13. The central controller 13 is electrically connected to or in communication connection with the preparation device 11 and the differential mobility analyzing device 12, wherein the preparation device 11 and the differential mobility analyzing device 12 of the beta2-microglobulin concentration analyzing system 1*b* may be the same as the preparation device 11 and the differential mobility analyzing device 12 shown in FIG. 1, and description thereof are not repeated herein. The central controller 13 is, for example, a computer. The central controller 13 may output a notification after the preparation device 11 finishing the preparation of the sample, to notify laboratory personnel to transfer the sample to the differential mobility analyzing device 12. After the differential mobility analyzing device 12 receives the sample, the central controller 13 may control the differential mobility analyzing device 12 to perform analysis on the sample. Specifically, methods of the central controller 13 determining that the differential mobility analyzing device 12 has received the sample may include: determining that the differential mobility analyzing device 12 has received the sample based on a confirmation command that laboratory personnel inputted to the central controller 13; and/or the central controller 13 is connected to a sensing element (for example, a pressure sensor, a RFID sensor etc.) of a latching member of the differential mobility analyzing device 12, and the central controller 13 determining that the differential mobility analyzing device 12 has received the sample when the sensing element is triggered.

Figure 3:
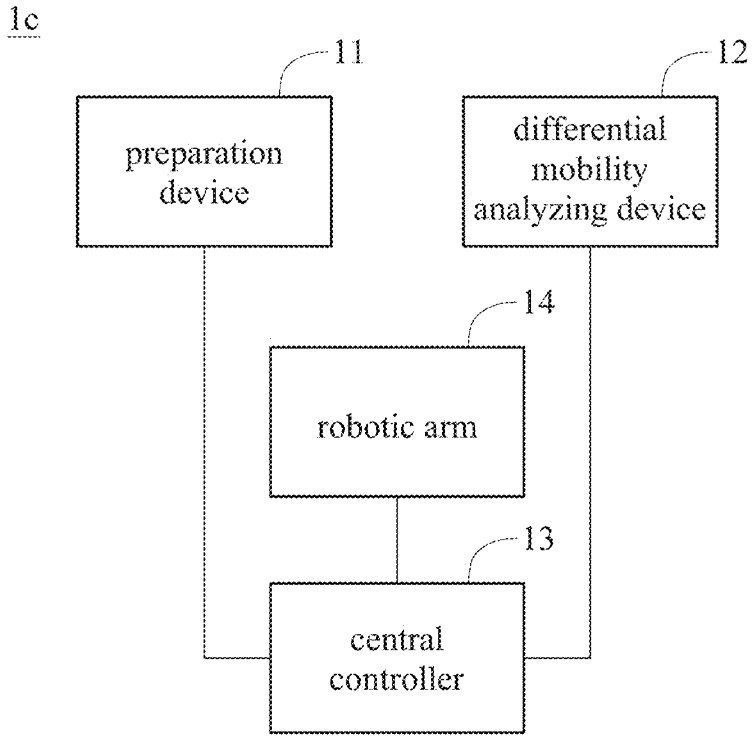
FIG. 3 is a block diagram illustrating a beta2-microglobulin concentration analyzing system according to yet another embodiment of the present disclosure.

Please refer to FIG. 3, wherein FIG. 3 is a block diagram illustrating a beta2-microglobulin concentration analyzing system according to yet another embodiment of the present disclosure. The beta2-microglobulin concentration analyzing system 1*c* shown in FIG. 3 includes the preparation device 11, the differential mobility analyzing device 12, the central controller 13 and a robotic arm 14. The central controller 13 is electrically connected to or in communication connection with the preparation device 11, the differential mobility analyzing device 12 and the robotic arm 14, wherein the preparation device 11, the differential mobility analyzing device 12 and the central controller 13 of the beta2-microglobulin concentration analyzing system 1*c* may be the same as the preparation device 11, the differential mobility analyzing device 12 and the central controller 13 shown in FIG. 2, and description thereof are not repeated herein. The central controller 13 may be configured to control movement of the robotic arm 14, to control the robotic arm 14 to transfer a centrifuge tube loaded with dialysate to the preparation device 11, the central controller 13 may monitor the process of preparing the sample, and control the robotic arm 14 to transfer the sample to the differential mobility analyzing device 12 after the preparation of the sample is finished.

The beta2-microglobulin concentration analyzing systems shown in FIG. 1-FIG. 3 may be configured to prepare the sample with the dialysate, and configured to analyze the beta2-microglobulin concentration of the sample.

Figure 4:
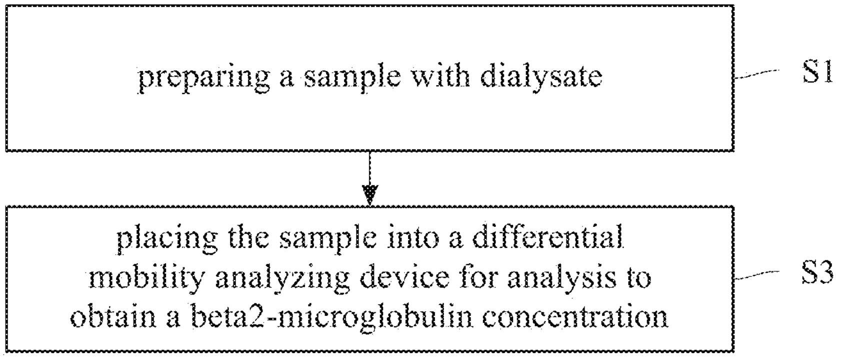
FIG. 4 is a flowchart illustrating a beta2-microglobulin concentration analyzing method according to an embodiment of the present disclosure.

Please refer to FIG. 1 and FIG. 4, wherein FIG. 4 is a flowchart illustrating a beta2-microglobulin concentration analyzing method according to an embodiment of the present disclosure. As shown in FIG. 4, the beta2-microglobulin concentration analyzing method includes: step S1: preparing a sample with dialysate; and step S3: placing the sample into a differential mobility analyzing device for analysis to obtain a beta2-microglobulin concentration.

The preparation device 11 may include, for example, a centrifuge machine for filtering out impurity in the dialysate in step S1 to obtain the sample. In step S3, the laboratory personnel places the sample into the differential mobility analyzing device 12 for analysis to obtain the beta2-microglobulin concentration. Accordingly, the beta2-microglobulin concentration of the dialysate may be obtained with lower costs.

Figure 5:
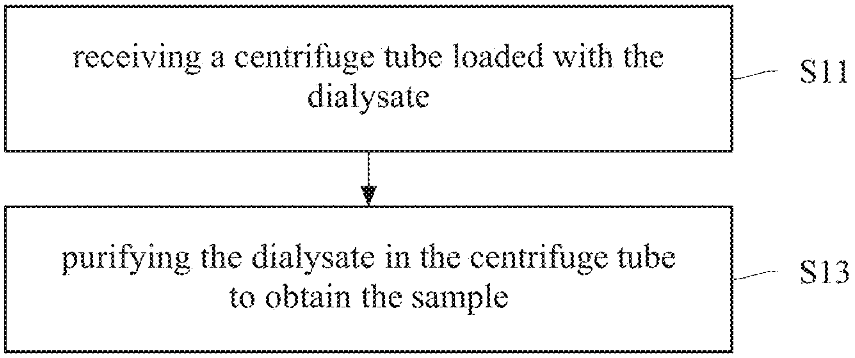
FIG. 5 is a detailed flowchart illustrating step S1 of FIG. 4.

To explain the method of the preparation device 11 preparing the sample in more detail, please refer to FIG. 1 and FIG. 5, wherein FIG. 5 is a detailed flowchart illustrating step S1 of FIG. 4. As shown in FIG. 5, step S1 of FIG. 4 may include: step S11: receiving a centrifuge tube loaded with the dialysate; and step S13: purifying the dialysate in the centrifuge tube to obtain the sample.

In step S11, the laboratory personnel loads the dialysate into the centrifuge tube, and places the centrifuge tube into the preparation device 11 (for example, the centrifuge machine). In step S13, the laboratory personnel operates the preparation device 11 to centrifuge the centrifuge tube loaded with the dialysate to remove impurity from the dialysate, thereby obtaining the sample for analyzing the beta2-microglobulin concentration.

Figure 6:
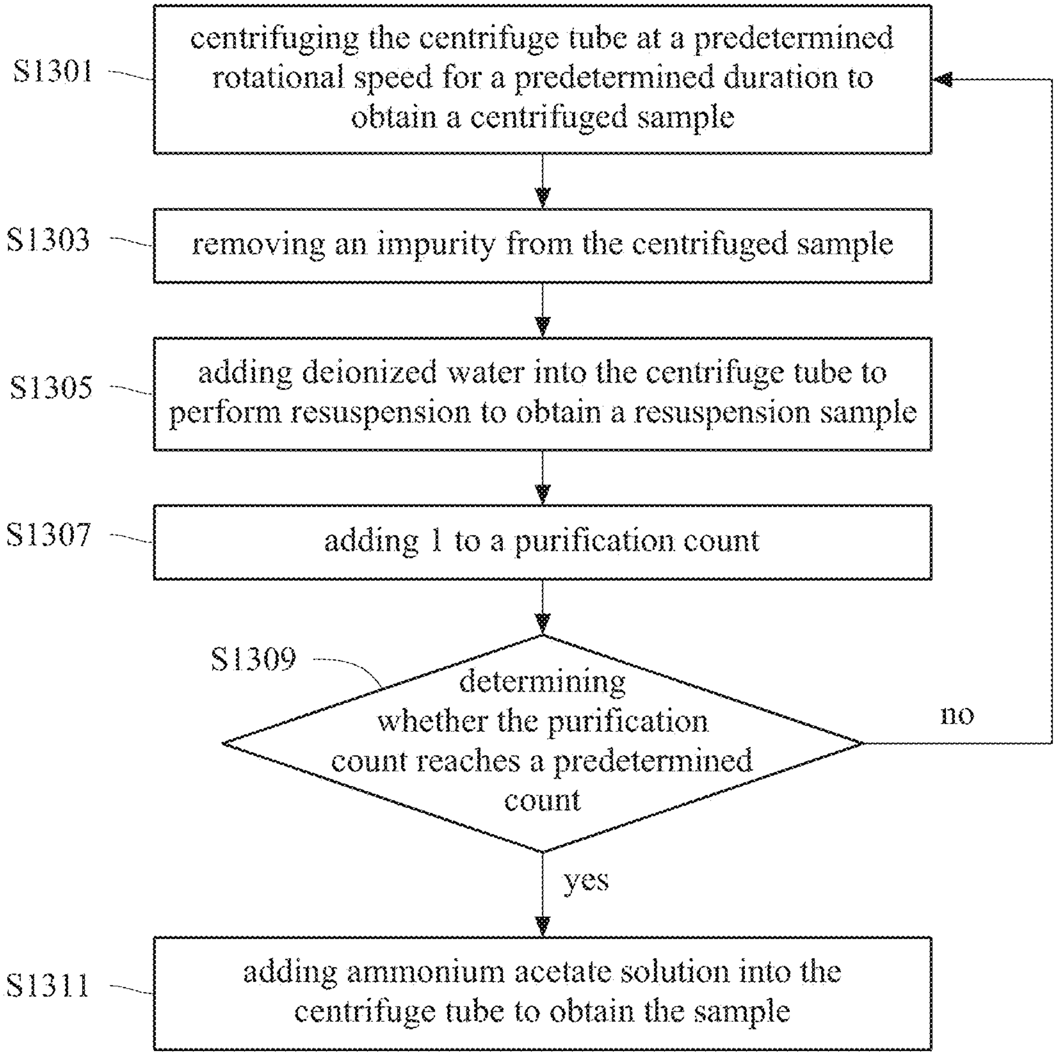
FIG. 6 is a detailed flowchart illustrating step S13 of FIG. 5 according to an embodiment of the present disclosure.
Figure 7:
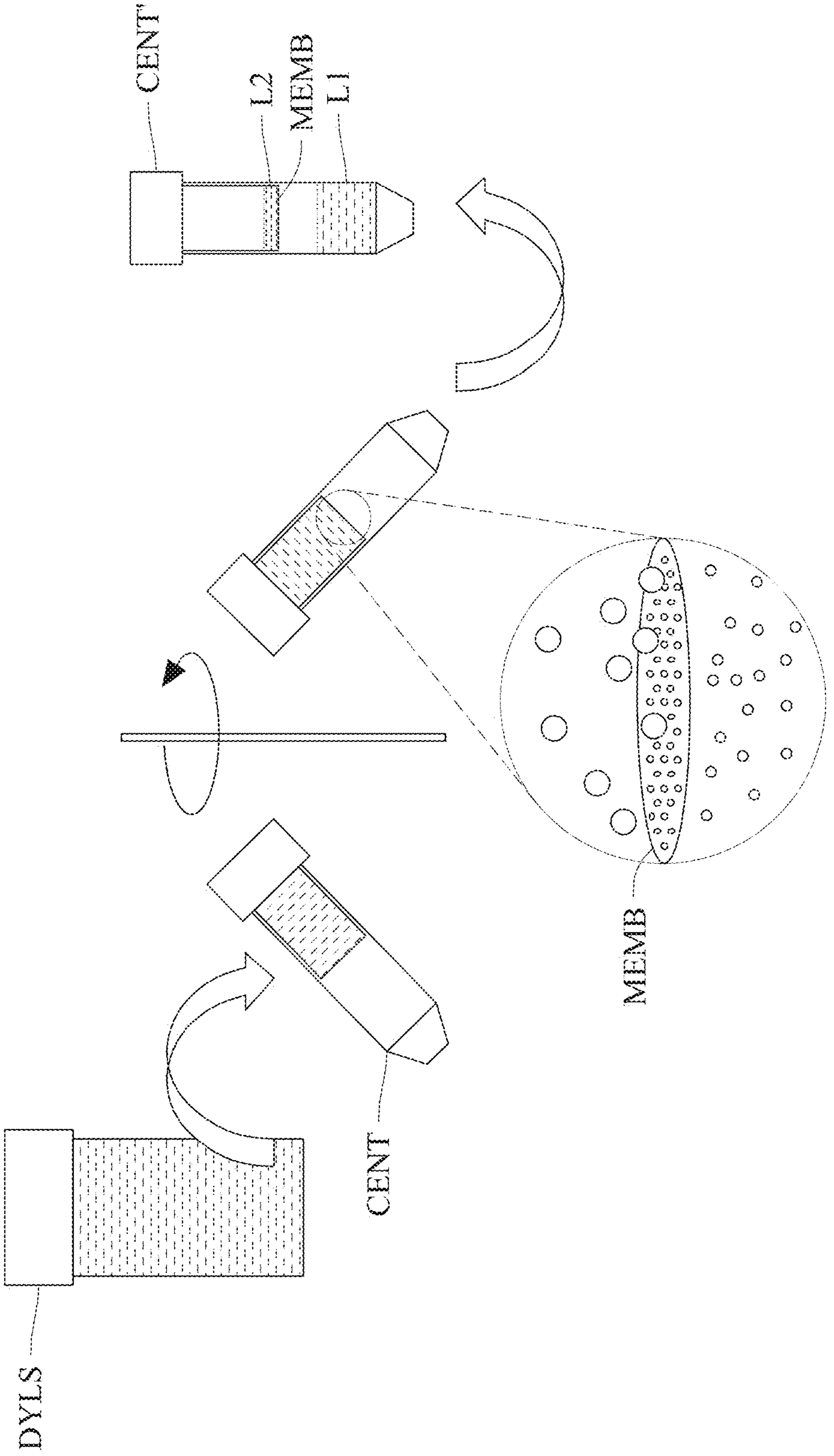
FIG. 7 is a schematic diagram illustrating a purification procedure.

To further explain method of the preparation device 11 preparing the sample, and method of purifying the dialysate loaded in the centrifuge tube, please refer to FIG. 3, FIG. 6 and FIG. 7, wherein FIG. 6 is a detailed flowchart illustrating step S13 of FIG. 5 according to an embodiment of the present disclosure, and FIG. 7 is a schematic diagram illustrating a purification procedure. As shown in FIG. 6, step S13 of FIG. 5 may include: step S1301: centrifuging the centrifuge tube at a predetermined rotational speed for a predetermined duration to obtain a centrifuged sample; step S1303: removing an impurity from the centrifuged sample; step S1305: adding deionized water into the centrifuge tube to perform resuspension to obtain a resuspension sample; step S1307: adding 1 to a purification count; step S1309: determining whether the purification count reaches a predetermined count; if the determination result of step S1309 is "yes", performing step S1311: adding ammonium acetate solution into the centrifuge tube to obtain the sample; and if the determination result of step S1309 is "no", adding the deionized water into the centrifuge tube again to perform resuspension to obtain another resuspension sample, and performing step S1301 on the another resuspension sample. The purification procedure may include step S1301 to S1309 shown in FIG. 6.

The predetermined rotational speed is, for example, fourteen thousand rotations per minute (14 krpm), and the predetermined duration is, for example, 15 minutes. In step S1301, the laboratory personnel may operate the preparation device 11 to perform centrifugation on the centrifuge tube CENT loaded with the dialysate DYLS at the predetermined rotational speed, wherein the centrifuge tube CENT may include a filtration membrane MEMB, and molecular weight cut off (MWCO) of the filtration membrane MEMB may be 3 kD.

After centrifugation, the centrifuged sample in the centrifuge tube CENT' may have layers, including an impurity layer L1 and a filtered layer L2 above the filtration membrane MEMB. The impurity layer L1 is the part that needs to be removed, and the filtered layer L2 is the part that needs to be kept. In step S1303, the laboratory personnel may use pipette to remove the impurity layer L1 from the centrifuged sample.

Then, in step S1305, the laboratory personnel adds deionized water into the centrifuged sample where impurity is already removed, to perform resuspension on the centrifuged sample with added deionized water to obtain the resuspension sample. The volume of the deionized water added into the centrifuge tube may be 500 μL. In step S1307, the central controller 13 may count a purification count. That is, the central controller 13 may add 1 to the purification count to record a number of times of performing resuspension, wherein an initial value of the purification count may be 0.

In step S1309, the laboratory personnel may determine whether the purification count reaches the predetermined count, wherein the predetermined count is, for example, 5. If the purification count reaches the predetermined count, the laboratory personnel performs step S1311, to add the ammonium acetate solution into the centrifuged sample containing deionized water, wherein a concentration of the ammonium acetate solution may be 20 mM. If the purification count does not reach the predetermined count, the laboratory personnel adds the deionized water into the centrifuge tube again to perform resuspension to obtain another resuspension sample, and performs the purification procedure on the another resuspension sample. Said "reach" herein refers to a situation of being equal to or larger than.

In short, step S1301 to step S1305 may be performed repeatedly for multiple times, wherein said multiple times equals to the predetermined count. When a number of times of performing step S1301 to step S1305 reaches the predetermined count, the laboratory personnel adds the ammonium acetate solution into the resuspension sample, to obtain the sample used for analyzing the beta2-microglobulin concentration, and the impurity concentration of the sample at this stage is less than 50 ppm.

It should be noted that, the present disclosure does not limit the order of performing step S1305, S1307 and S1309, as long as step S1307 is performed prior to step S1309. In addition, numerical values of the predetermined rotational speed, the predetermined duration, volume of the deionized water, the purification count, the predetermined count and concentration of the ammonium acetate solution described in the embodiment of FIG. 6 is merely an example, the present disclosure does not limit the actual numerical values of these parameters.

Figure 8:
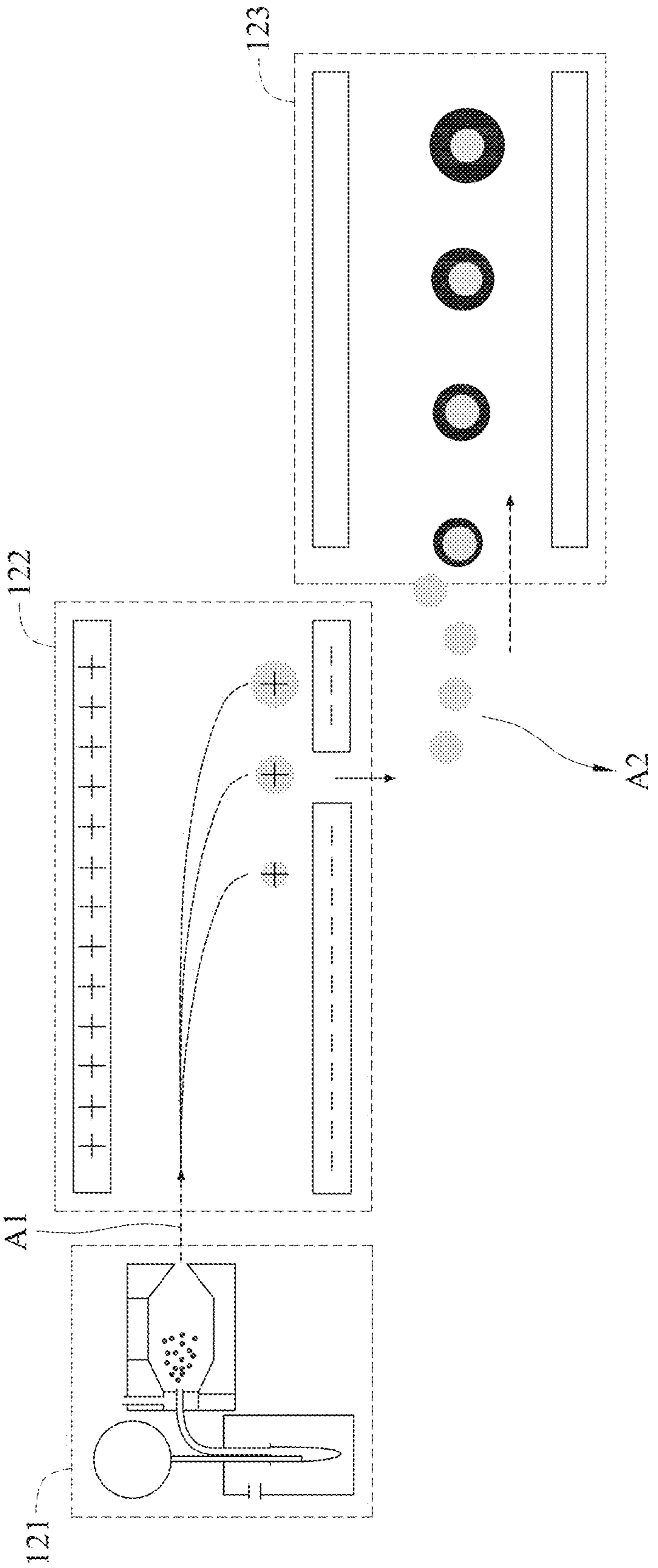
FIG. 8 is a schematic diagram illustrating a beta2-microglobulin concentration analyzing device according to an embodiment of the present disclosure.
Figure 9:
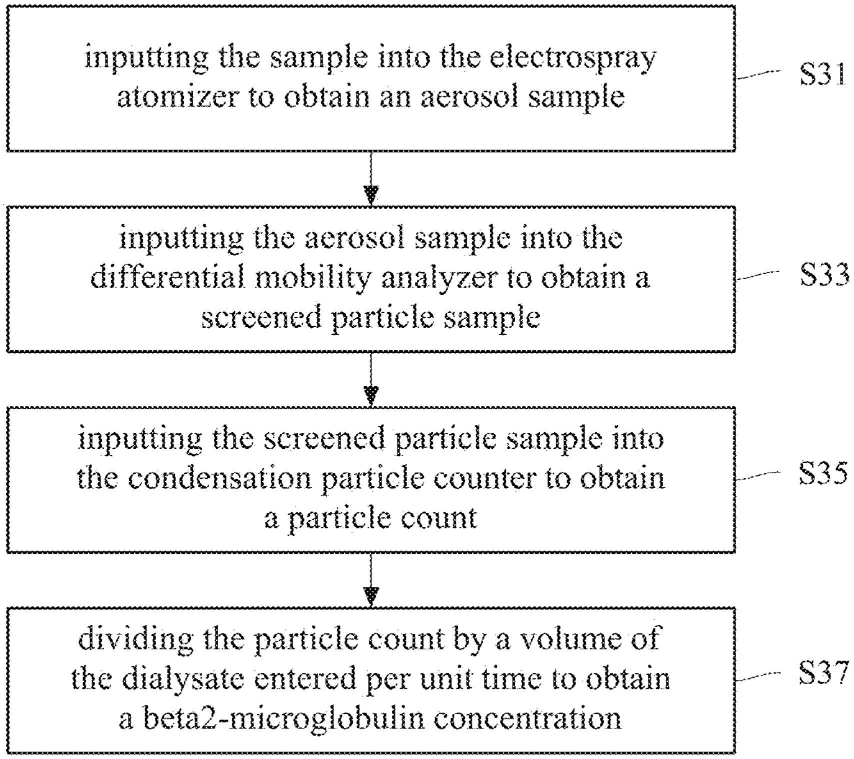
FIG. 9 is a diagram illustrating a beta2-microglobulin concentration analyzing method according to an embodiment of the present disclosure.

Please refer to FIG. 3, FIG. 8 and FIG. 9, wherein FIG. 8 is a schematic diagram illustrating a beta2-microglobulin concentration analyzing device according to an embodiment of the present disclosure, and FIG. 9 is a diagram illustrating a beta2-microglobulin concentration analyzing method according to an embodiment of the present disclosure. The differential mobility analyzing device 12 shown in FIG. 8 may be used to implement the differential mobility analyzing device 12 shown in FIG. 1 to FIG. 3, and the steps shown in FIG. 9 may be used to implement step S3 in FIG. 4.

As shown in FIG. 8, the differential mobility analyzing device 12 according to an embodiment of the present disclosure may include an electrospray atomizer 121, a differential mobility analyzer 122 and a condensation particle counter (CPC) 123. For example, the model number of the electrospray atomizer 121 may be TSI-3480; the model number of the differential mobility analyzer 122 may be TSI-3080; and the model number of the condensation particle counter 123 may be TSI-3776, but the present disclosure is not limited thereto.

The sample outlet of the electrospray atomizer 121 may be connected to the sample inlet of the differential mobility analyzer 122, and the sample outlet of the differential mobility analyzer 122 may be connected to the sample inlet of the condensation particle counter 123. Alternatively, the laboratory personnel or the robotic arm may transfer the sample produced by the electrospray atomizer 121 to the differential mobility analyzer 122 for analysis, and then transfer the sample produced by the differential mobility analyzer 122 to the condensation particle counter 123 for counting particle number.

As shown in FIG. 9, step S3 shown in FIG. 2 may include: step S31: inputting the sample into the electrospray atomizer to obtain an aerosol sample; step S33: inputting the aerosol sample into the differential mobility analyzer to obtain a screened particle sample; step S35: inputting the screened particle sample into the condensation particle counter to obtain a particle count; and step S37: dividing the particle count by a volume of the dialysate entered per unit time to obtain a beta2-microglobulin concentration.

In step S31, the electrospray atomizer 121 may receive the prepared sample from the preparation device 11, and apply a positive voltage to the sample for the electrosprayed liquid sample to produce positively charged aerosol sample A1, wherein an aerosol flowrate driven by the electrospray atomizer 121 may be 1.5 liters per minute (1.5 L/min), but the present disclosure does not limit the actual numerical value of the aerosol flowrate. In step S33, the laboratory personnel transfers the aerosol sample A1 from the electrospray atomizer 121 to the differential mobility analyzer 122, thereby selecting the screened particle sample A2 from the positively charged the aerosol sample A1. The screened particle sample A2 has a specified protein molecular weight and a specified protein size, and the specified protein molecular weight is, for example, 11.8 kD, and a range of the specified protein size is, for example, 3.85 nm to 4.14 nm. A sheath flowrate of the differential mobility analyzer 122 may be 20 liters per minute (20 L/min). The present disclosure does not limit the actual numerical values of the specified protein molecular weight, the specified protein size and the sheath flowrate.

In step S35, the laboratory personnel transfers the screened particle sample A2 from the differential mobility analyzer 122 to the condensation particle counter 123. The condensation particle counter 123 may be equipped with a laser optical detector, to calculate a number of particles with the specified protein molecular weight and the specified protein size through laser light. The laser wavelength of the condensation particle counter 123 may be 405 nm. The size of beta2-microglobulin (3.85 nm) is far smaller than a size range that is detectable by laser light. Therefore, general laser optical detector might not be suitable for beta2-microglobulin analysis of the present disclosure. The beta2-microglobulin screened by the differential mobility analyzer 122 should be condensed and grown on the particle surface to enlarge the size of beta2-microglobulin from 3.85 nm to micron level (>1 μm) before it can be used in the measurement and metering performed by the laser optical detector, which illustrates the necessity of using the condensation particle counter 123. In step S37, the laboratory personnel may divide the particle count of the screened particle sample A2 by the volume the dialysate loaded per unit time to obtain the beta2-microglobulin concentration. Step S37 may also be performed by the central controller 13.

Figure 10A:
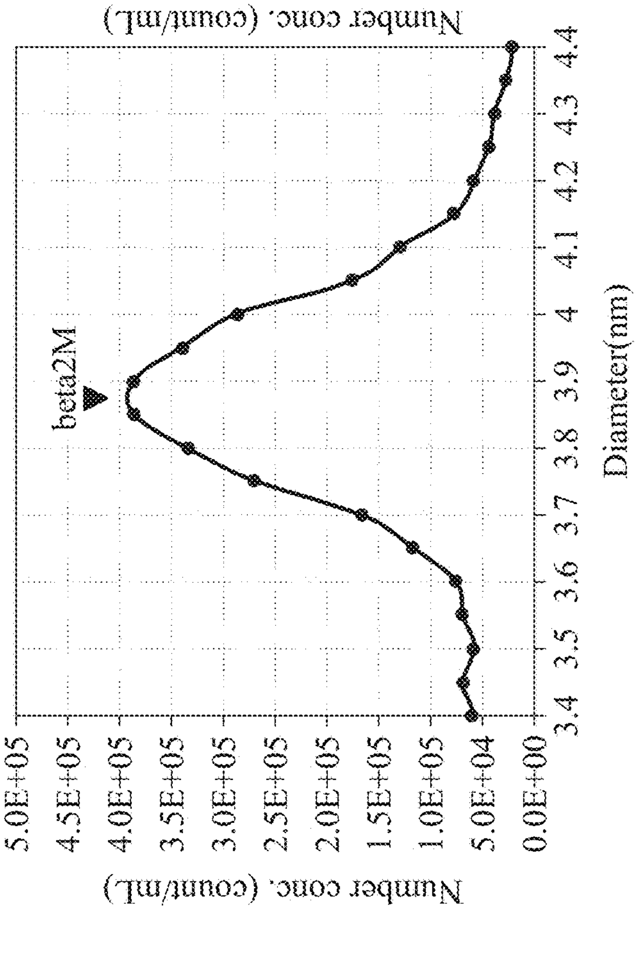
FIG. 10*a* shows a test result of reference beta2-microglobulin concentration of commercial sample.
Figure 10B:
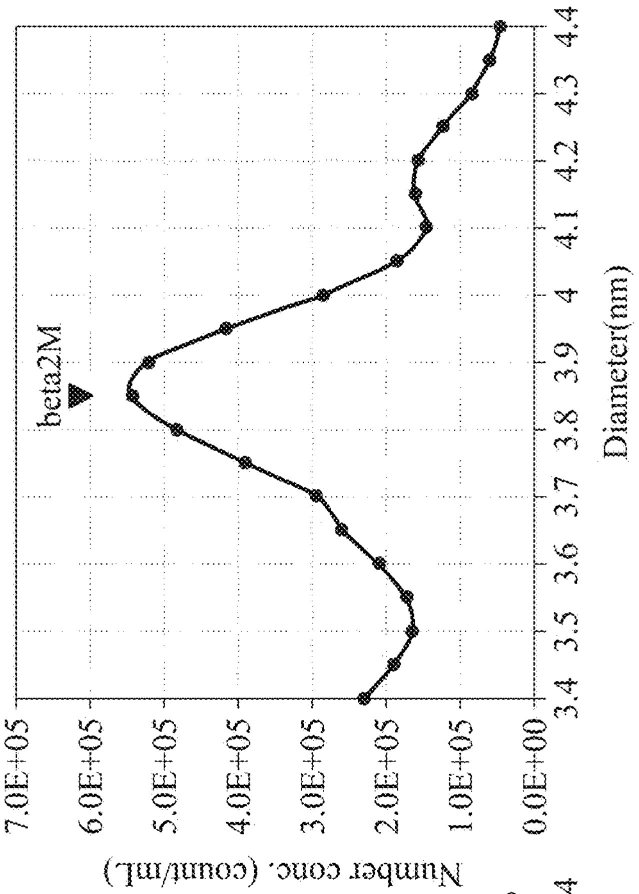
FIG. 10*b* shows a test result of beta2-microglobulin concentration according to one or more embodiments of the present disclosure.

Please refer to FIG. 10*a* and FIG. 10*b*, wherein FIG. 10*a* shows a test result of reference beta2-microglobulin concentration of commercial sample, FIG. 10*b* shows a test result of beta2-microglobulin concentration according to one or more embodiments of the present disclosure.

It can be seen from FIG. 10*a* that, the result of the beta2-microglobulin concentration of commercial sample indicates a maximum concentration value at around 3.85 nm (marked by "beta2M" in FIG. 10*a*), meaning the size (diameter) of beta2-microglobulin is around 3.85 nm. It can be seen from FIG. 10*b* that, the result of the beta2-microglobulin concentration obtained according to one or more embodiments of the present disclosure also shows a maximum concentration value at around 3.85 nm (marked by "beta2M" in FIG. 10*b*). Therefore, FIG. 10*a* and FIG. 10*b* show that the sample prepared by the beta2-microglobulin concentration analyzing method and system according to one or more embodiments of the present disclosure has sufficiently high beta2-microglobulin purity.

Figure 11B:
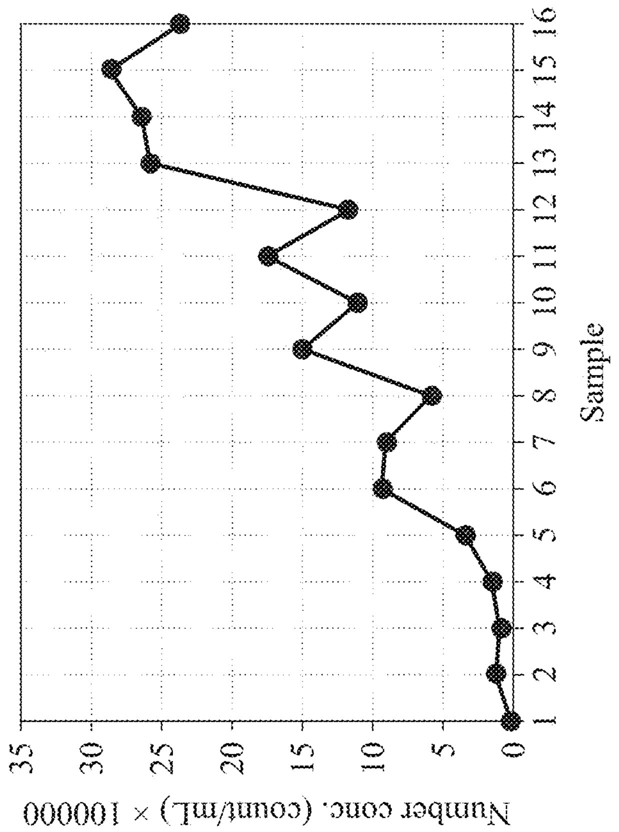
FIG. 11*b* shows a result of beta2-microglobulin concentration according to one or more embodiments of the present disclosure.
Figure 11A:
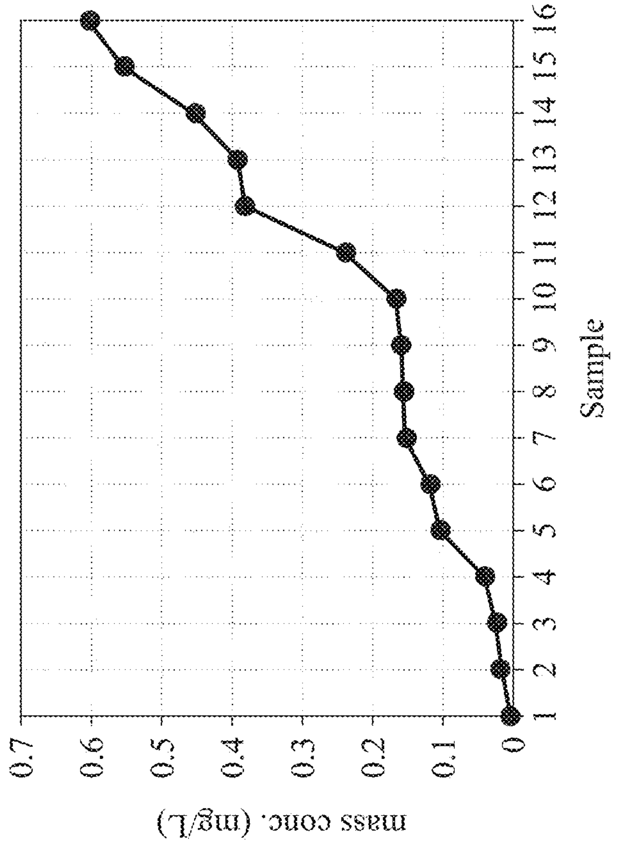
FIG. 11*a* shows a result of beta2-microglobulin concentration of 16 samples using ELISA.

Please refer to FIG. 11*a* and FIG. 11*b*, wherein FIG. 11*a* shows a result of beta2-microglobulin concentration of 16 samples using ELISA, FIG. 11*b* shows a result of beta2-microglobulin concentration according to one or more embodiments of the present disclosure, and FIG. 11*a* and FIG. 11*b* show test results of 16 samples prepared according to one or more embodiments of the present disclosure.

As seen from FIG. 11*a* and FIG. 11*b*, the results obtained using ELISA and the results obtained using the beta2-microglobulin concentration analyzing method and system according to one or more embodiments of the present disclosure are in accordance with each other. Comparing to the beta2-microglobulin concentration analyzing method and system of the present disclosure, using ELISA for analysis requires additional antibodies and chemical substances. Therefore, FIG. 11*a* and FIG. 11*b* show that the beta2-microglobulin concentration analyzing method and system according to one or more embodiments of the present disclosure may be used to obtain an accurate result with lower cost.

It should be noted that, the beta2-microglobulin concentration analyzing method according to one or more embodiments of the present disclosure are explained using the beta2-microglobulin concentration analyzing system 1*a* shown in FIG. 1, but said method may also be performed by the beta2-microglobulin concentration analyzing system 1*b* shown in FIG. 2 or the beta2-microglobulin concentration analyzing system 1*c* shown in FIG. 3. Specifically, in an embodiment where the method is performed by the beta2-microglobulin concentration analyzing system 1*b*, the central controller 13 may pre-store operating parameters (for example, the predetermined rotational speed and the predetermined duration) of the preparation device 11 and operating parameters (for example, the aerosol flowrate, the specified protein molecular weight, the specified protein size, the sheath flowrate and the laser wavelength) of the differential mobility analyzing device 12, so that the preparation device 11 and the differential mobility analyzing device 12 may process the sample according to the operating parameters after the laboratory personnel loads the sample into the preparation device 11 and the differential mobility analyzing device 12. The preparation device 11 and the differential mobility analyzing device 12 may output notification to a terminal device (for example, a computer, a mobile device etc.) at the laboratory personnel's end to notify the laboratory personnel to transfer the sample that has been processed and analyzed. In an embodiment where the method is performed by the beta2-microglobulin concentration analyzing system 1*c*, the central controller 13 may also pre-store operating parameters of the preparation device 11 and the differential mobility analyzing device 12, and the central controller 13 controls the robotic arm 14 to place the sample into the preparation device 11 and the differential mobility analyzing device 12, and controls the operation of the preparation device 11 and the differential mobility analyzing device 12 according to the operating parameters after the sample is placed into the preparation device 11 and the differential mobility analyzing device 12.

In other words, in the embodiment of FIG. 1, transferring the sample, removing impurity from the sample, controlling the operation of the preparation device 11 and the differential mobility analyzing device 12 and determining the purification count are performed by the laboratory personnel; in the embodiment of FIG. 2, transferring the sample and removing impurity from the sample are performed by the laboratory personnel, and determining the purification count and controlling the operation of the preparation device 11 and the differential mobility analyzing device 12 may be performed by the central controller 13; in the embodiment of FIG. 3, transferring the sample and removing impurity from the sample may be performed by the robotic arm 14 which is controlled by the central controller 13, and controlling the operation of the preparation device 11 and the differential mobility analyzing device 12 as well as determining the purification count may be performed by the central controller 13.

In view of the above description, the beta2-microglobulin concentration analyzing method and device according to one or more embodiments of the present disclosure may lower the cost of analyzing the beta2-microglobulin concentration of the dialysate and lower time spent on sample preparation, processing and analysis, and an accurate result may be obtained. In addition, the beta2-microglobulin concentration analyzing method and device according to one or more embodiments of the present disclosure may allow the particle count of screened beta2-microglobulin to be obtained by using the condensation particle counter.

What is claimed is:

1. A beta2-microglobulin concentration analyzing method, adapted to a differential mobility analyzing device, wherein the differential mobility analyzing device comprises an electrospray atomizer, a differential mobility analyzer and a condensation particle counter, and the method comprises:
- inputting a sample of dialysate into the electrospray atomizer to obtain an aerosol sample;
- inputting the aerosol sample into the differential mobility analyzer to obtain a screened particle sample;
- inputting the screened particle sample into the condensation particle counter to obtain a particle count; and
- dividing the particle count by a volume of the dialysate sample entered per unit time to obtain a beta2-microglobulin concentration,
- wherein the sample of dialysate is subjected to a purification procedure that comprises:
  - centrifuging a centrifuge tube loaded with the sample of dialysate at a predetermined rotational speed for a predetermined duration to obtain a centrifuged sample;
  - removing an impurity from the centrifuged sample;
  - adding deionized water into the centrifuge tube to perform resuspension to obtain a resuspension sample;
  - adding 1 to a purification count; and
  - determining whether the purification count reaches a predetermined count;
- if the purification count reaches the predetermined count, adding ammonium acetate solution into the centrifuge tube to obtain the resuspension sample; and if the purification count does not reach the predetermined count, adding the deionized water into the centrifuge tube again to perform resuspension to obtain another resuspension sample, and performing the purification procedure on the another resuspension sample.

2. The beta2-microglobulin concentration analyzing method according to claim 1, wherein a protein size of the screened particle sample ranges from 3.85 nm to 4.14 nm, a protein molecular weight of the screened particle sample is 11.8 kD.

3. The beta2-microglobulin concentration analyzing method according to claim 1, wherein a laser wavelength of the condensation particle counter is 405 nm.

4. A beta2-microglobulin concentration analyzing device, comprising:

an electrospray atomizer configured to receive a sample of dialysate and output an aerosol sample;

a differential mobility analyzer configured to receive the aerosol sample and output a screened particle sample; and a condensation particle counter configured to receive the screened particle sample and output a particle count, wherein beta2-microglobulin concentration is obtained by dividing the particle count by a volume of the dialysate sample entered per unit time, wherein the sample of dialysate is subjected to a purification procedure comprises that:

centrifuging a centrifuge tube loaded with the sample of dialysate at a predetermined rotational speed for a predetermined duration to obtain a centrifuged sample;

removing an impurity from the centrifuged sample;

adding deionized water into the centrifuge tube to perform resuspension to obtain a resuspension sample;

adding 1 to a purification count; and determining whether the purification count reaches a predetermined count;

if the purification count reaches the predetermined count, adding ammonium acetate solution into the centrifuge tube to obtain the resuspension sample; and if the purification count does not reach the predetermined count, adding the deionized water into the centrifuge tube again to perform resuspension to obtain another resuspension sample, and performing the purification procedure on the another resuspension sample.

5. The beta2-microglobulin concentration analyzing device according to claim 4, further comprising:

a robotic arm; and a central controller connected to the electrospray atomizer, the differential mobility analyzer, the condensation particle counter and the robotic arm, the central controller configured to control the robotic arm to place the sample of dialysate into the electrospray atomizer, move the aerosol sample from the electrospray atomizer to the differential mobility analyzer, and move the screened particle sample to the condensation particle counter.

6. The beta2-microglobulin concentration analyzing device according to claim 4, wherein a protein size of the screened particle sample ranges from 3.85 nm to 4.14 nm, a protein molecular weight of the screened particle sample is 11.8 kD.

7. The beta2-microglobulin concentration analyzing device according to claim 4, wherein a laser wavelength of the condensation particle counter is 405 nm.

* * * * *